United States Patent [19]

Koza

[11] Patent Number: 4,773,131

[45] Date of Patent: Sep. 27, 1988

[54] CLAMPING DEVICE

[75] Inventor: Josef Koza, Berlin, Fed. Rep. of Germany

[73] Assignee: Geza Heidt, Fed. Rep. of Germany

[21] Appl. No.: 922,048

[22] Filed: Oct. 22, 1986

[30] Foreign Application Priority Data

Oct. 23, 1985 [DE] Fed. Rep. of Germany ....... 3538202

[51] Int. Cl.$^4$ .............................................. A44B 21/00
[52] U.S. Cl. ....................................... 24/459; 24/523; 24/564
[58] Field of Search ................. 24/459, 483, 536, 564, 24/489, 523, 529; 128/325

[56] References Cited

U.S. PATENT DOCUMENTS

| 1,915,764 | 6/1933 | Schnabel | 24/489 |
|---|---|---|---|
| 3,509,882 | 5/1970 | Blake | 24/564 |
| 3,757,031 | 9/1973 | Izraeli | 24/459 |
| 3,760,811 | 9/1973 | Andrew | 24/459 |
| 4,340,996 | 7/1982 | Starace | 24/459 |
| 4,408,924 | 10/1983 | Huebner | 24/459 |
| 4,536,926 | 8/1985 | Pantaleo | 24/523 |
| 4,538,373 | 9/1985 | Rogers | 24/489 |

Primary Examiner—Victor N. Sakran
Attorney, Agent, or Firm—McGlew and Tuttle

[57] ABSTRACT

The invention relates to a clip consisting of two clamping jaws 1, 2 provided with actuating elements 3, 4 and, in particular, molded of plastic, and of an elastic element which joins the former and presses them together in the clamping plane 5. To make secure clamping of an object to be retained between the clamping jaws 1, 2 possible, it is provided that the actuating elements 3, 4 are disposed so as to be slidable in a plane oriented perpendicular to the clamping plane 5 against the action of the elastic element 6 and that the actuating ends 15, 16 of each actuating element 3, 4 project beyond the rear end 17, 18 of the respectively other actuating element 3, 4. This causes the clamping jaws 1, 2 to open and close in a direction oriented exactly perpendicular to the clamping plane 5, thereby making secure clamping of objects possible.

5 Claims, 1 Drawing Sheet

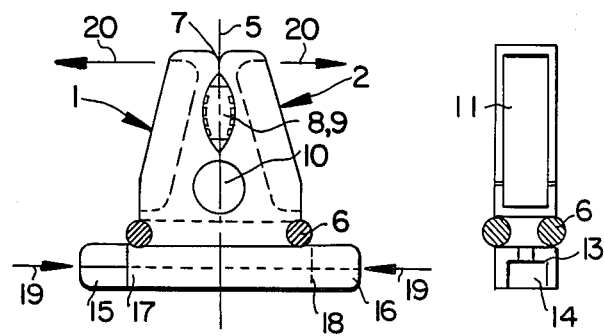
FIG. 1
FIG. 2
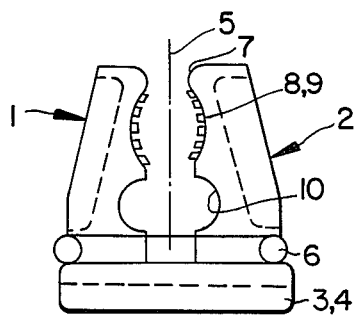
FIG. 3
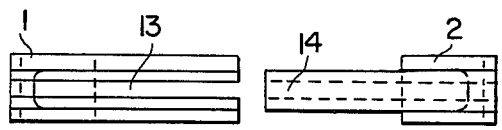
FIG. 6  FIG. 9
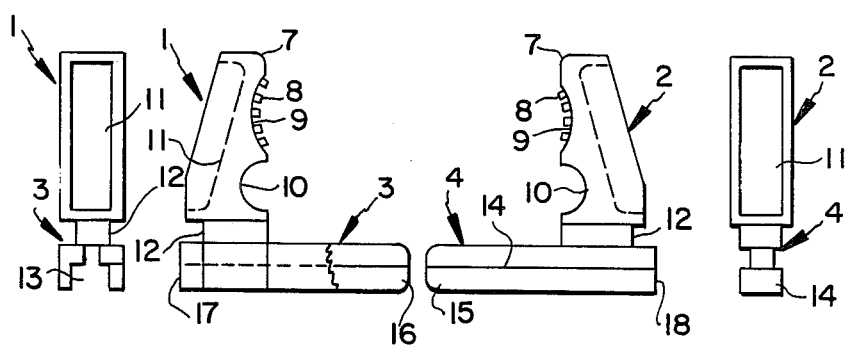
FIG. 5  FIG. 4  FIG. 7  FIG. 8

CLAMPING DEVICE

The invention relates to a clip according to the preamble of patent claim 1. Such clips are in general use, e.g. as clothes pins, surgical clamps clips for textile sheets, paper clips, as clips for photographic purposes, for shop window decorations, as binder for documents and the like.

The conventional clip, also called clothes pin, consists of clamping jaws provided with actuating elements, in particular of wood or plastic. A metallic spring is used as elastic element to hold and press the known clip together. The clip opens by pressing together the two clip handles serving as actuating elements and closes after the release of the clip handles so that the object located between the clamping jaws is compressed by means of the spring. Of disadvantage in the known clips is the assembly of the two clamping jaws equipped with the actuating elements by means of the specially shaped spring, the bent spring ends of which must be inserted in outer slots in both clamping jaws, the spring body itself being located between the two clamping jaws, forming the pivoting axis of the two clamping jaws.

Another disadvantage is that the pressure of the two clamping jaws acts wedgelike, i.e. having the tendency to push the object to the clamped out of the space between the clamping jaws. For this reason, the clamping action of the known clip is uncertain. Furthermore, when compressing thicker objects, the two clamping jaws can be lifted off the actual body of the spring so that the latter hang freely, without guidance, between the two clamping jaws. There is yet another disadvantage relating to the plastic clip which, due to a material weakening necessitated by the arrangement of the spring, easily breaks in its pivoting axis, i.e. in the area between clamping jaw and actuating element.

Therefore, it is an object of the invention to design a clip of the kind described so that greater stability on the one hand and a reliable clamping action of the clamping jaws on the other are achieved.

The solution of this problem is found in the characterizing features of patent claim 1. The clip according to the invention no longer works with pivotability of the clamping jaws relative to each other, but with a rectiliniear motion of the clamping jaws toward each other so that the object to be compressed is held securely. The action direction is exactly perpendicular to the clamping plane. An opening motion of the clip according to the invention is also perpendicular to the clamping plane. The actuating ends of each actuating element projecting beyond the rear end of the respectively other actuating element being pushed against each other, thus effecting the opening of the clip in a direction perpendicular to the clamping plane through a strictly sliding motion.

In the preferred embodiment, one actuating element is provided with a guide slot, located in the sliding plane, for a guide web of the other actuating element slidably guided in the guide slot. To open and close the clip, a relative motion of the guide web and guide slot takes place, bringing about the parallel pressure at the clamping jaws.

In further preferred embodiment of the invention, holding the clamping jaws together is accomplished by a rubber ring which acts as elastic element and is seated in a circling groove in a neck part between the clamping jaws and the actuating elements.

The sliding motion of the clamping jaws of the actuating elements guarantees a parallel, uniform pressure of the clamping jaws, maintained also in the same force and direction when the objects to be compressed are of different thickness.

A particular advantage of the clip design according to the invention is that the clamping jaws may be of any desired length, depending on the application, without encountering difficulties with the design of the actuating elements. In the clips preknown from the state of the art, the length of the handles serving as actuating elements must always equal approximately the length of the clamping jaws, as measured from the pivot point of the preknown clip.

The clamping jaws provided with the actuating elements are expediently produced of plastic injection molding material. Polystyrol has proved to be especially advantageous.

The invention is explained below by way of an embodiment example illustrated in the drawings which show in FIG. 1 a front view of the closed clip,
FIG. 2 a side view thereof,
FIG. 3 a front view of the open clip,
FIG. 4 a front view of the left clamping jaw with actuating element with a gudie slot,
FIG. 5 a side view thereof,
FIG. 6 a bottom view,
FIG. 7 a front view of the right clamping jaw with actuating element with guide web.
FIG. 8 a side view therief, and
FIG. 9 a side view thereof.

The clip consists of two clamping jaws 1, 2, each provided with an actuating element 3 and 4, respectively, and with an elastic element in the form of a rubber ring 6 pressing the actuating elements 3, 4 together in the clamping plane 5. With the exception of the actuating elements 3, 4, the clamping jaws 1, 2, are identical and comprise pressure areas 7 pressing against each other in the clamping plane 5 and, adjacent thereto, troughs 9 provided with teeth 8 and, below them, semicircular recesses 10 which, when used as laundry pin, for instance, serve the accomodation of the laundry line not shown. On their outsides, the clamping jaws 1, 2, have cutouts 11 to save weight.

Below the semicircular recesses 10 there is formed in the area of a neck part between the clamping jaws 1, 2 and the associated actuating elements 3, 4 a groove 12 which serves the seating of a rubber ring 6 as detailed in FIGS. 1 through 3.

The clamping jaw 1 shown on the left of each of these FIGURES includes the actuating element 3 which extends in a plane perpendicular to the clamping plane 5 and forms a forklike sliding element (FIG. 6) with a guide slot 13 which may be seen especially in FIG. 5. The guide slot 13 is T-shaped in cross-section and extends transversely through the actuating element 3, also passing through below the clamping jaw 1.

The clamping jaw 2 shown on the right in the FIGURES has the actuating element 4 which is oriented perpendicular to the clamping plane 5 and designed as T-shaped guide web 14 shown in particular in FIG. 8 and also extending below the clamping jaw 2.

Both the clamping jaw 1 shown on the left of the FIGURES with the associated actuating element 3 and the clamping jaw 2 shown on the right of the FIG- URES with its associated actuating element 4 are each molded integrally of plastic, in particular by injection molding.

As FIG. 1 shows, to assemble the clip, the guide web 14 of the right clamping jaw 2 is pushed into the guide slot 13 of the left clamping jaw 1, the actuating end 15 of the guide web 14 of the right clamping jaw 2 projecting out of the rear end 17 of the left clamping jaw 1, as shown in FIG. 1. Analogously, the actuating end 16 of the actuating element 3 projects to the right beyond the rear end 18 of the right clamping jaw 2, as likewise shown in FIG. 1. Then the rubber ring 6 is inserted in the groove 12 over the clamping jaws 1, 2. The clip can be opened by exerting a finger pressure, e.g. by thumb and index finger, in the direction of the arrows 19 (FIG. 1) so that the clamping jaws 1, 2 are each moved apart in the direction of the arrows 20. The maximum opening width is reached when the outer contour of the actuating ends 15, 16 covers the rear ends 17, 18 of the respective actuating elements 3, 4.

In an embodiment not detailed, the actuating elements 3, 4 may also be provided with handling projections, protruding in the direction of the clamping plane 5 under the actuating elements 3, 4 so that a greater opening width can be obtained.

The length of the clamping jaws 1, 2 is freely selectable and can be adapted to the length required for the respective application.

I claim:

1. A clamp comprising first and second clamping jaws each having an abutting clamping face meeting in a common plane and having an opposite face with a lower end having a recess therein spaced from said lower end, each of said clamping jaws having a finger contacting portion below said recess projecting outwardly beyond the ends of said recess, one of said clamping jaws having a receiving slide extending transversely to said common plane and the other of said jaws having a guide web slidable in said receiving slide, said guide web and said receiving slide having contact portions which cause separation of said jaws when said slide and said contact portions are moved together relatively beyond the predetermined amount, a resilient ring member engaged in said recess around said jaws and biasing said jaws to a closed position with said jaw clamping faces interengage, said jaws being separable to open them by pushing said guide web and said slide together, to separate said jaws.

2. A clamp according to claim 1, wherein said clamping jaws have a clamping face with an intermediate trough in each face leaving a recess, said clamping jaw each having teeth projecting into said recess.

3. A clamp according to claim 1, wherein said first and second clamping jaws each have an abutting clamping face with a semicircular recess which, when said clamping jaws are closed, are aligned.

4. Clamp consisting of two clamping jaws, in particular formed of plastic, provided with actuating elements, and of an elastic element connecting said jaws and pressing them together in the clamping plane, the actuating elements being arranged slidable in a plane oriented perpendicular to the clamping plane counter to the action of the plastic element, characterized in that the one actuating element is provided with a guiding groove in the sliding plane, while the other actuating end is provided with a guiding web slidingly guided therein, that the cross-section of guiding groove and guiding web is T-shaped, that the actuating end of each actuating element protrudes over the rear end or respectively of the respective other actuating element and that as elastic element there is provided a rubber ring received in a peripheral groove in a neck portion between the clamping jaws and the actuating elements.

5. Clamp according to claim 4, characterized in that the actuating elements are provided with gripping lugs which protrude in the direction of the clamping plane from under the actuating elements.

* * * * *